(12) United States Patent  (10) Patent No.: US 8,551,077 B2
Main et al.  (45) Date of Patent: Oct. 8, 2013

(54) HANDLE FOR A SURGICAL INSTRUMENT AND SURGICAL INSTRUMENT ASSEMBLY

(75) Inventors: David Main, Leeds (GB); Anna Sophia Hellinga, Apeldoorn (NL); Peter Moran, Leeds (GB)

(73) Assignee: Surgical Innovations Limited, Leeds, West Yorkshire (GB)

( * ) Notice: Subject to any disclaimer, the term of this patent is extended or adjusted under 35 U.S.C. 154(b) by 195 days.

(21) Appl. No.: 12/919,576

(22) PCT Filed: Feb. 27, 2009

(86) PCT No.: PCT/GB2009/050203
§ 371 (c)(1),
(2), (4) Date: Aug. 26, 2010

(87) PCT Pub. No.: WO2009/106898
PCT Pub. Date: Sep. 3, 2009

(65) Prior Publication Data
US 2011/0009850 A1     Jan. 13, 2011

(30) Foreign Application Priority Data
Feb. 29, 2008 (GB) .................................. 0803773.1

(51) Int. Cl.
*A61B 17/00* (2006.01)
(52) U.S. Cl.
USPC .................. 606/1; 606/205; 606/208; 81/393
(58) Field of Classification Search
USPC ............... 606/1, 205–208, 174, 209; 81/315, 81/385, 393
See application file for complete search history.

(56) References Cited

U.S. PATENT DOCUMENTS

| 5,176,702 | A | * | 1/1993 | Bales et al. | 606/208 |
| 5,472,451 | A | | 12/1995 | Freitas | |
| 5,947,996 | A | * | 9/1999 | Logeman | 606/205 |
| 6,436,122 | B1 | * | 8/2002 | Frank et al. | 606/208 |

(Continued)

FOREIGN PATENT DOCUMENTS

| DE | 4322602 | 2/1994 |
| DE | 4428479 | 2/1996 |

(Continued)

OTHER PUBLICATIONS

International Search Report for PCT/GB2009/050203, ISA/EP, Rijswijk, NL, mailed Jul. 30, 2009.

(Continued)

*Primary Examiner* — Sam Yao
*Assistant Examiner* — Nathan J Jenness
(74) *Attorney, Agent, or Firm* — Harness, Dickey & Pierce, P.L.C.

(57) ABSTRACT

A handle for a surgical instrument used in keyhole, endoscopic, and laparoscopic surgery, having a pivoting or articulated end portion and a mechanism for indexing the pivoting movement of the end portion. The indexing mechanism allows adjustment of the angle of the end portion for improved control and tactile feedback to the user. The handle also has a mechanism for locking and unlocking movement of the end portion whereby the end portion can be pivoted or articulated to a desired angle and the locking mechanism moved to a position to prevent movement of the end portion, thus holding it at the desired angle to achieve the improved control and tactile feedback to the user.

12 Claims, 7 Drawing Sheets

(56) References Cited

U.S. PATENT DOCUMENTS

| | | |
|---|---|---|
| 7,090,689 B2 | 8/2006 | Nagase et al. |
| 7,753,904 B2 | 7/2010 | Shelton, IV et al. |
| 2003/0009854 A1 | 1/2003 | Shippert |
| 2006/0287642 A1* | 12/2006 | Perlin ............................. 606/1 |
| 2007/0299469 A1 | 12/2007 | Carpenter et al. |
| 2008/0125762 A1 | 5/2008 | Hiller |

FOREIGN PATENT DOCUMENTS

| | | |
|---|---|---|
| DE | 202008014698 | 4/2009 |
| EP | 1250891 | 10/2002 |
| EP | 1813212 | 8/2007 |
| JP | 63-147449 | 6/1988 |
| JP | 2011-192233 | 7/1999 |
| JP | 2007-537803 | 12/2007 |
| NL | 1012856 C | 2/2001 |
| WO | 2005/112795 | 12/2005 |
| WO | 2008/002574 | 1/2008 |

OTHER PUBLICATIONS

UK Search Report for priority document GB0803773.1, established Jun. 4, 2008.
Japanese Office Action mailed Jun. 4, 2013 for Japanese Serial No. 2010-548196, with included translation.

* cited by examiner

HANDLE FOR A SURGICAL INSTRUMENT AND SURGICAL INSTRUMENT ASSEMBLY

CROSS-REFERENCE TO RELATED APPLICATIONS

This application is a 371U.S. National Stage of International Application No. PCT/GB2009/050203, filed Feb. 17, 2009. This application claims the benefit of United Kingdom Patent Application No. GB 0803773.1, filed Feb. 29, 2008. The disclosures of the above applications are incorporated herein by reference.

The present invention relates to a handle for use with surgical instruments and in particular to a handle for use with keyhole surgery, endoscopic and laparoscopic instruments. The present application also relates to a surgical instrument assembly and system including such a handle.

Keyhole surgery, endoscopic and laparoscopic techniques are known and have been developed to allow surgery with smaller incisions than were previously the case. In general the techniques require the insertion of a long, slender instrument into a body cavity via a small incision. The instruments may comprise an endoscope for visualising the body cavity and one or more other instruments for carrying out a surgical procedure, for example a biopsy.

Surgical instruments for use in these techniques are controlled by a handle attached to the shaft of the instrument. The handle allows the surgeon to manipulate the instrument and operate it as required. One form of handle which is in widespread use comprises two members that can pivot relative to one another to operate the instrument. The members typically define openings for receiving a surgeon's digits, so they can be moved in the same way as scissors. For example, the pivoting movement of the members may be converted into movement of jaws at the end of the surgical instrument. A feature of a pivotal connection is that the two members move relative to one another in the same plane.

In use the handle may have to be moved into a position where the arc of relative movement of the two members is in a plane which is not comfortable for the surgeon's wrist. For example the surgeon's wrist may need to be rotated to an extreme angle. It is desirable to avoid this.

In an effort to solve this problem a handle where one of the members is articulated, having an end portion that can pivot laterally relative to the plane of the arc of relative movement has been proposed in NL-C-1012856. This articulation has been found to improve the ergonomics of the handle and reduce the likelihood of a surgeon's wrist being at an extreme angle. U.S. Pat. No. 5,472,451 (Freitas et al) also discusses an endoscopic hand held grip including a pivot portion through which the thumb of the operator is received. However, the applicant has found that the movement of the end portion or pivot portion makes the control less predictable and reduces the feedback received by the surgeon from the instrument in use. As a result, some surgeons have preferred to use handles without articulated or pivoting components, despite the problems with rotation of the wrist to sometimes extreme angles.

It would be desirable to provide a handle for a surgical instrument in which rotation of the user's wrist to extreme angles is avoided, while retaining good feedback and control for the user.

In one aspect, the present invention provides a handle for a surgical instrument comprising one part with a pivoting or articulated end portion, and a means for indexing the pivoting movement of the end portion. The applicant has found that the indexing means allows adjustment of the angle of the end portion together with improved control and tactile feedback to the user, compared with not including the indexing means.

In another aspect, the present invention provides a handle for a surgical instrument comprising one part with a pivoting or articulated end portion, and a means for locking the movement of the end portion. The applicant has found that the locking means, when in a position to prevent movement of the end portion, improves control and tactile feedback. In use the locking would typically be disengaged while the user positions the instrument, and engaged to prevent movement of the end portion before operating the instrument.

According to the present invention there is provided a handle for a surgical instrument, the handle comprising:
  a first part comprising:
    a main portion; and
    an end portion which is pivotally connected to the main portion;
  a second part which is pivotally connected to the main portion of the first part such that the first and second parts can move relative to each other; and
  an indexing means for limiting the movement of the end portion to predetermined positions relative to the main portion and for retaining the end portion in one of the predetermined positions.

The first and second parts may comprise openings for receiving a users digits. The pivotal connection of the second part to the main portion may have an axis which is substantially perpendicular to the axis of the pivotal connection between the main portion and the end portion. Any suitable way of connecting the parts to provide pivotal movement may be utilised. For example, the pivotal connection between the end portion and main portion may be implemented by a pin joint, or by a flexible connecting strip that enables relative pivotal movement by its flexing.

The relative movement of the first and second parts results in the operation of a surgical instrument connected to the handle. The indexing means allows adjustment of the angle of the end portion together with improved control and tactile feedback to the user, compared with the prior art. The indexing means acts to retain the end portion in a predetermined position, reducing the chance of the end portion moving relative to the main portion during operation of a surgical instrument.

The indexing means may be an indexing mechanism. In one embodiment the indexing means comprises a series of depressions spaced apart from each other formed in the main portion. A bearing is retained in the end portion, and is resiliently biased towards the main portion so that it engages one of the series of depressions to provide the indexing.

In one embodiment the bearing is substantially spherical, this allows it to move more easily from one depression to the next. Other bearing shapes, such as cylindrical, are also suitable.

In one embodiment the handle further comprises a locking means configured to be movable between locked and unlocked positions. In the locked position the end portion is prevented from moving relative to the main portion. This allows a further improvement to the user's control of the handle and the feedback received. The locking means may be a locking mechanism.

According to another aspect of the invention, there is provided a handle for a surgical instrument, the handle comprising:
  a first part comprising:
    a main portion; and
    an end portion which is pivotally connected to the main portion;

a second part which is pivotally connected to the main portion of the first part such that the first and second parts can move relative to each other; and a locking means configured to be movable between locked and unlocked positions, and wherein in the locked position the end portion is prevented from moving relative to the main portion.

The locking means provides an improvement in the tactile feedback and control of the handle over prior art handles without locking.

The locking means may be a locking mechanism. One embodiment of the locking means comprises a shaft having a longitudinal projection configured to engage a corresponding recess formed in the end portion and, in the locked position, to also engage a corresponding recess formed in the main portion. With this embodiment, the construction may be simplified if the shaft also forms the axis about which the end portion pivots relative to the main portion.

In an alternative embodiment the locking means comprises a slider provided on the end portion, wherein the slider has a protrusion that, in the locked position, engages a corresponding recess formed in the main portion. This enables locking to be provided with a simple construction.

The handle may further comprise a ratchet means for allowing movement of the first part towards the second part and for resisting movement of the first part away from the second part. This is particularly useful if the surgical instrument to which the handle is attached exerts a resilient force, for example jaws which are closed against a resilient force, such as might be provided by a spring. The ratchet means may be a ratchet mechanism.

The handle may further comprise a trigger configured to engage a pawl of the ratchet means and for disengaging the ratchet when pressed. The handle may further comprise a ratchet disengaging lever connected to the trigger and movable between a first position, in which the trigger must be pressed to disengage the ratchet, and a second position, in which the ratchet is disengaged.

The ratchet disengaging lever is substantially flush with the surface of the trigger when in the second position, which improves the ergonomics of the handle in use. A further advantage of this construction is that it allows a ratchet disengaging lever to be provided on a part of the handle that moves relative to the surgical instrument operated by the handle. The lever must be able to move by a certain distance between the first and second positions to provide its function. In the first position the lever is closer to the parts of the handle that do not move relative to the tool. This restricts the space available for lever and can restrict the space for a user to place there finger on top of the lever to operate it. By folding the lever flush with the trigger in the second position, the space occupied in the first position is minimised allowing more space for a user to place their finger on top of it to operate it. This is particularly advantageous in the restricted space available when the lever is provided on a part of the handle that moves relative to the tool.

Advantageously, the ratchet disengaging lever comprises at least one extension for enabling a user to move the lever from the second position to the first position. The extension can extend beyond the surface of the trigger, so that when the ratchet disengaging lever is in the second position, flush with the surface of the trigger, a user can still easily operate the ratchet disengaging lever using the extension to move it back to the first position.

The design of the ratchet disengaging lever described above is therefore particularly suitable for handles in which the ratchet disengaging lever is mounted on a part of the handle that moves relative to the surgical instrument. In some embodiments, the features of the ratchet disengaging lever described above may be provided without locking or indexing means.

The handle of the present invention may be used in a surgical instrument assembly. The surgical instrument assembly may further comprise connection means for releasably connecting the surgical instrument to the handle. In that case, it can form of the basis of a surgical instrument system comprising various different handles and instruments. For example, the same handle may be used with different instruments, or an additional handle may be provided in addition to the handle of the present invention.

Embodiments of the present invention will now be described by way of example with reference to the accompanying drawings, in which like reference numerals indicate like parts, and in which.

Figure 1A:
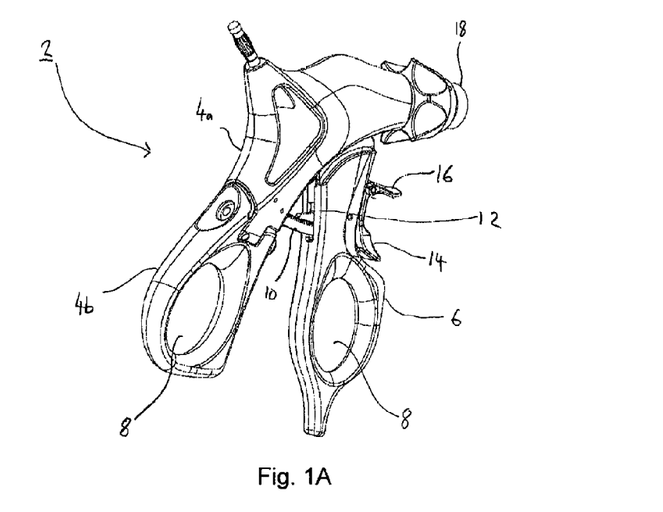
FIGS. 1A-C depict a perspective view of an embodiment of the present invention with an end portion at different orientations relative to a main portion.
Figure 2:
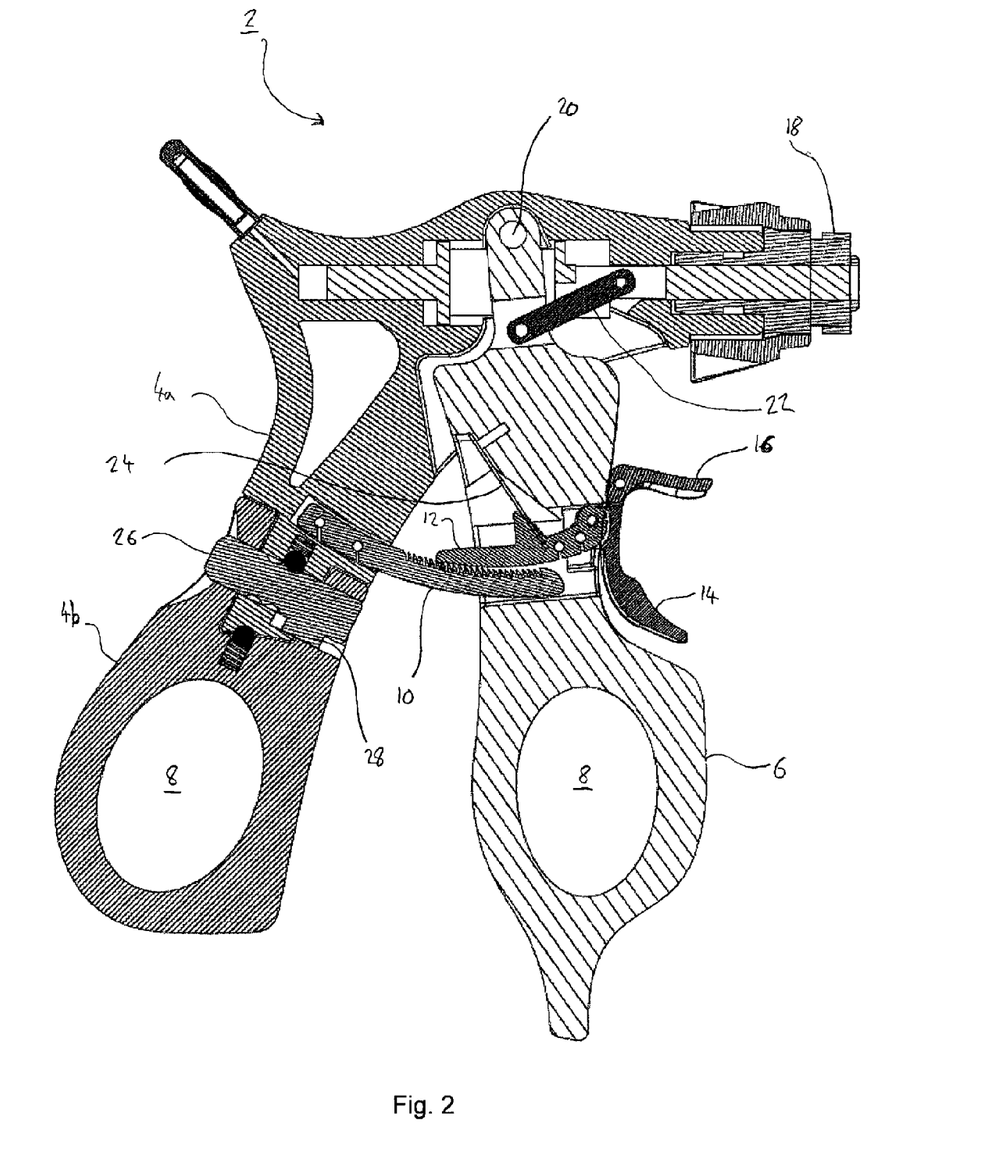
FIG. 2 depicts a cross section of the embodiment of FIGS. 1A-C.

FIG. 1A depicts a perspective view of an embodiment of the handle 2 of the present invention. A cross section of the embodiment of FIG. 1A is depicted in FIG. 2. The handle 2 comprises a first part and a second part 6 which are pivotally connected to each other. The first part comprises a main portion 4a and an end portion 4b pivotally connected to the main portion 4a. The axis of the pivotal connection between the end portion 4b and the main portion 4a is substantially perpendicular to the axis of the pivotal connection between the first part and the second part 6.

Figure 1B:
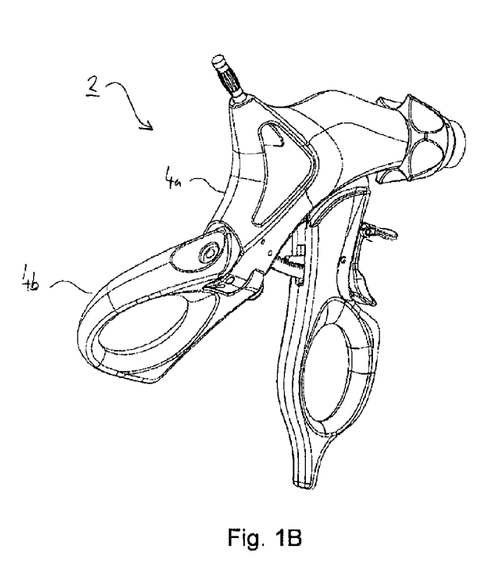
Figure 1C:
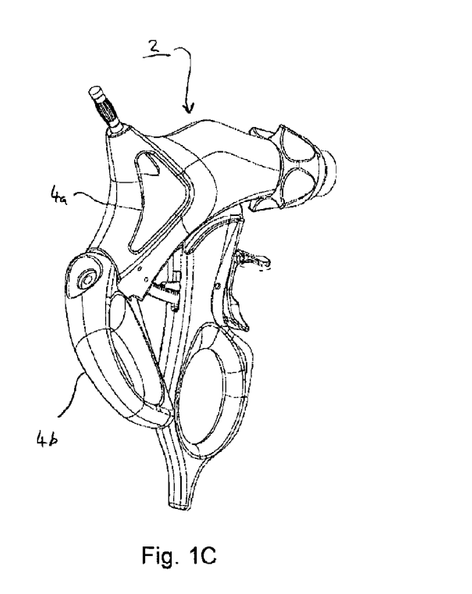

FIGS. 1B and 1C depict perspective views of the embodiment of FIG. 1A with the end portion 4b in different positions relative to the main portion 4a.

The second part 6 and the end portion 4b comprise openings 8, which are sized to receive on or more of a user's digits in use. Preferably, the openings 8 are sized so that a user can insert one or more fingers into the opening of the second part 6 and a thumb into the end portion 4b.

The handle also comprises a ratchet 10 and pawl 12 that act to allow movement of the second part 6 towards the first part but to resist the movement of the second part 6 away from the first part. A trigger 14 is provided on the second part 6 that, when pressed towards the first part by a user, acts on the pawl 12 to disengage it from the ratchet 10, allowing free movement of the second part 6 relative to the first part (both towards and away from the first part).

Figure 7A:
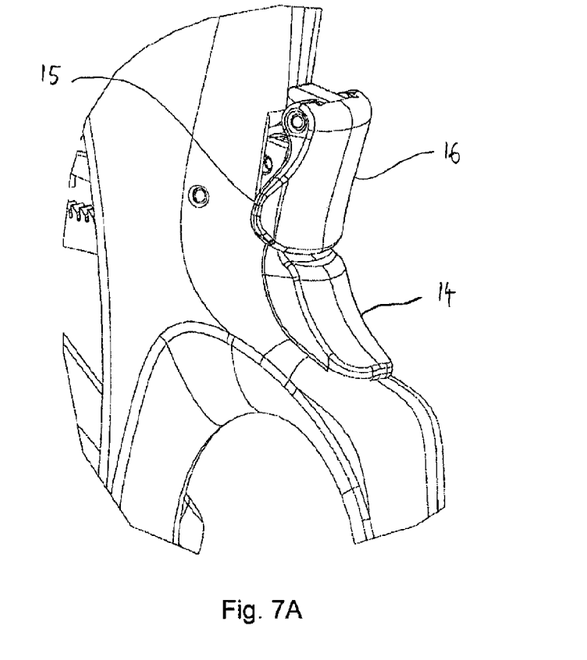
FIGS. 7A and 7B depict partial perspective views from different angles of a ratchet disengaging lever.
Figure 7B:
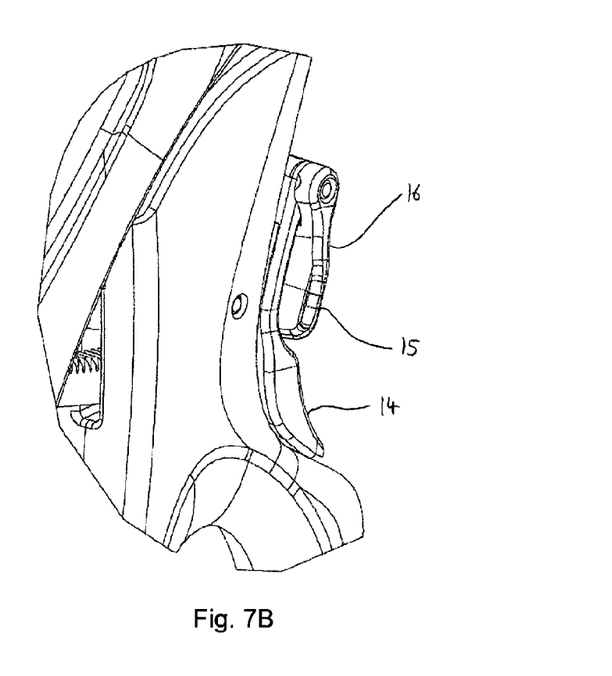

A ratchet disengaging lever 16 is provided on trigger 14. The ratchet disengaging lever 16 can be moved between a first position, away from the trigger 14 (as depicted in FIGS. 1A, 1B and 1C) and a second position where it rests against the surface of the trigger 14 (as depicted in FIGS. 7A and 7B). In the second position the ratchet disengaging lever is flush with the surface of the trigger 14.

The shape of the ratchet disengaging lever 16 can be seen more clearly in FIGS. 7A and 7B. These show partial perspective views of the handle from different angles. An extension 15 is formed on the ratchet disengaging lever 16 that projects beyond the surface of the trigger 14 when the ratchet disengaging lever 16 is in the second position. The extension 15 allows a user to move the ratchet disengaging lever out of the second position more easily—otherwise the flush position can make it difficult for a user to grasp the ratchet disengaging lever 16. The extension 15 is preferably provided on both sides, but could also be provided on one side only.

The handle 2 also has a connector 18 at it's distal end for connection of a surgical instrument. The connector is a ball and socket type connector, for example those used on tools and handles commercially available from Surgical Innovations Ltd.

As can be seen most clearly from the cross section of FIG. 2, the pivotal connection between the second part 6 and the main portion 4a of the first part is provided by a pin joint 20. The second part 6 is connected to a link 22 so that the rotational movement of the second part 6 relative to the main portion 20 is converted in a linear translation that can be transferred to a surgical instrument connected to the connector 18.

The cross section of FIG. 2 also shows the leaf spring 24 that provides a resilient force that urges the pawl 12 against the ratchet 10. The cam profile of the ratchet disengaging lever 16 is also visible, so that in the second position, folded flush with the trigger 14, the ratchet disengaging lever 16 acts against the pawl 12 to move it out of engagement with the ratchet 10.

Figure 3A:
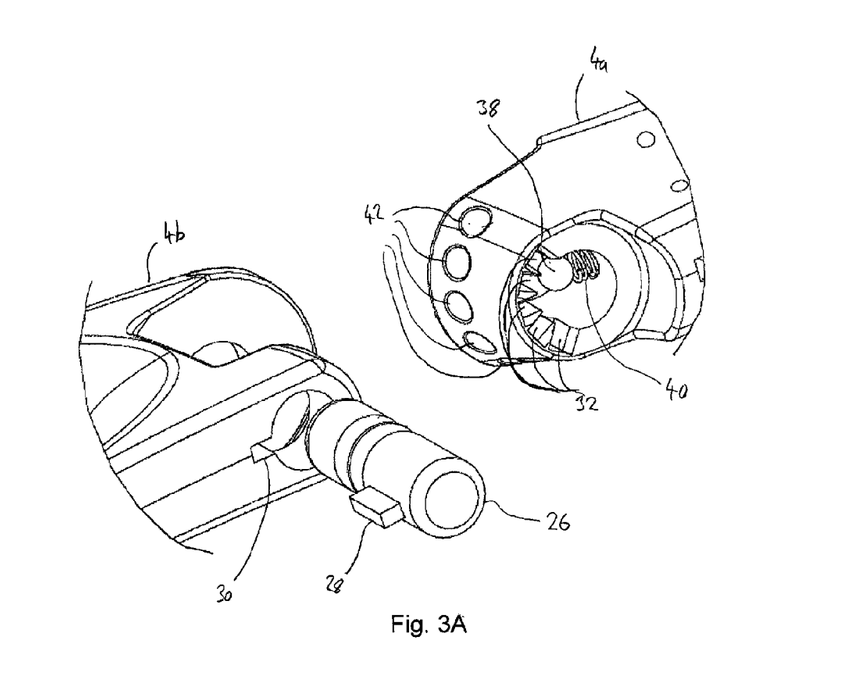
FIGS. 3A and 3B are exploded diagrams of a combined index and locking mechanism according to an embodiment of the present invention.
Figure 3B:
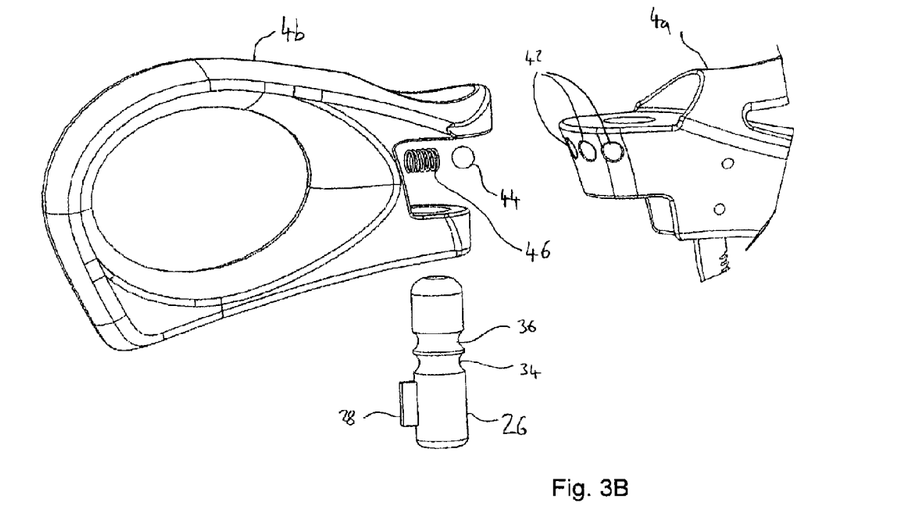

The embodiment comprises an indexing and a locking mechanism which will now be described with reference to the cross section of FIG. 2 and the exploded diagrams of FIGS. 3A and 3B.

A shaft 26 provides the pivotal connection between the end portion 4b and the main portion 4a. The shaft 26 has a projection 28 which extends from the surface of the shaft 26 and is oriented parallel to the longitudinal axis. The shaft engages corresponding recesses 30, 32 which are formed in the end portion 4b and the main portion 4a respectively.

Two circumferential grooves 34, 36 are formed in the surface of the shaft 26 which engage a ball bearing 38 retained in the main portion 4a. The ball bearing 38 is urged towards the grooves by a helical spring 40. The force of the ball bearing 38 against the shaft 26 holds it in place and allows for two positions of the shaft. In one position, with the ball bearing 38 engaged with groove 36, the shaft is positioned so that the projection 28 engages only recess 30, enabling pivotal movement between the end portion 4b and the main portion 4a. In a second position, with the ball bearing 38 engaged with groove 34, the shaft is positioned so that the projection 28 engages both the recess 30 of the end portion 4b and one of the recesses 32 formed in the main portion 4a, preventing relative movement of the end portion 4b and main portion 4a. The combination of the projection 28 and the recesses 30, 32 therefore forms a locking mechanism.

To provide indexing of the end portion position a plurality of depressions 42 are formed in the end portion. In this embodiment five depressions 42 are formed, although other embodiments may provide more or less than this. A ball bearing 44 is received in the end portion 4b and resiliently urged against the end of the main portion 4a by a helical spring 46. The ball bearing 44 is therefore urged into one of the depressions 42, engaging the depressions 42 to provide indexing. The resilient force from the helical spring 46 means that some force is required to compress the spring before the end portion 4b can be moved significantly relative to the main portion 4a. This provides a force to prevent movement of the end portion when the lock formed by the projection 28 on the shaft is not engaged.

The recesses 32 for locking the position of the end portion are formed at corresponding radial positions around the shaft 26 as the depressions 42. This enables the indexing to locate the end portion 4b into a position at which it can be locked easily, if required.

This handle of the embodiment is made from an injection-moulded high temperature polymer, although other manufacturing techniques and materials may also be used. For example the handle may be machined from medical-grade materials.

In use, it is envisaged that the user will initially deploy the handle 2 with the end portion 4b parallel with main portion 4a and the shaft 26 in the locked position. This ensures that the handle 2 can be used with good control and tactile feedback. If, during manoeuvring of the handle 2, this initial position causes a users wrist to be at an extreme angle, the shaft can be moved by a simple push action into the unlocked position. The end portion 4b is then moved to the desired position. The indexing mechanism provides resistance against movement out of the selected position and the handle can be operated in that position. For improved certainty that the end portion 4b will remain at the same position relative to the main portion 4a, the lock can optionally be engaged.

Thus, this embodiment allows a user to adjust the relative position of the end portion 4b to avoid a wrist being at an uncomfortable angle. In addition the indexing and locking enable the tool to have improved control and tactile feedback when the end portion 4b is not parallel to the main portion 4a.

Figure 4:
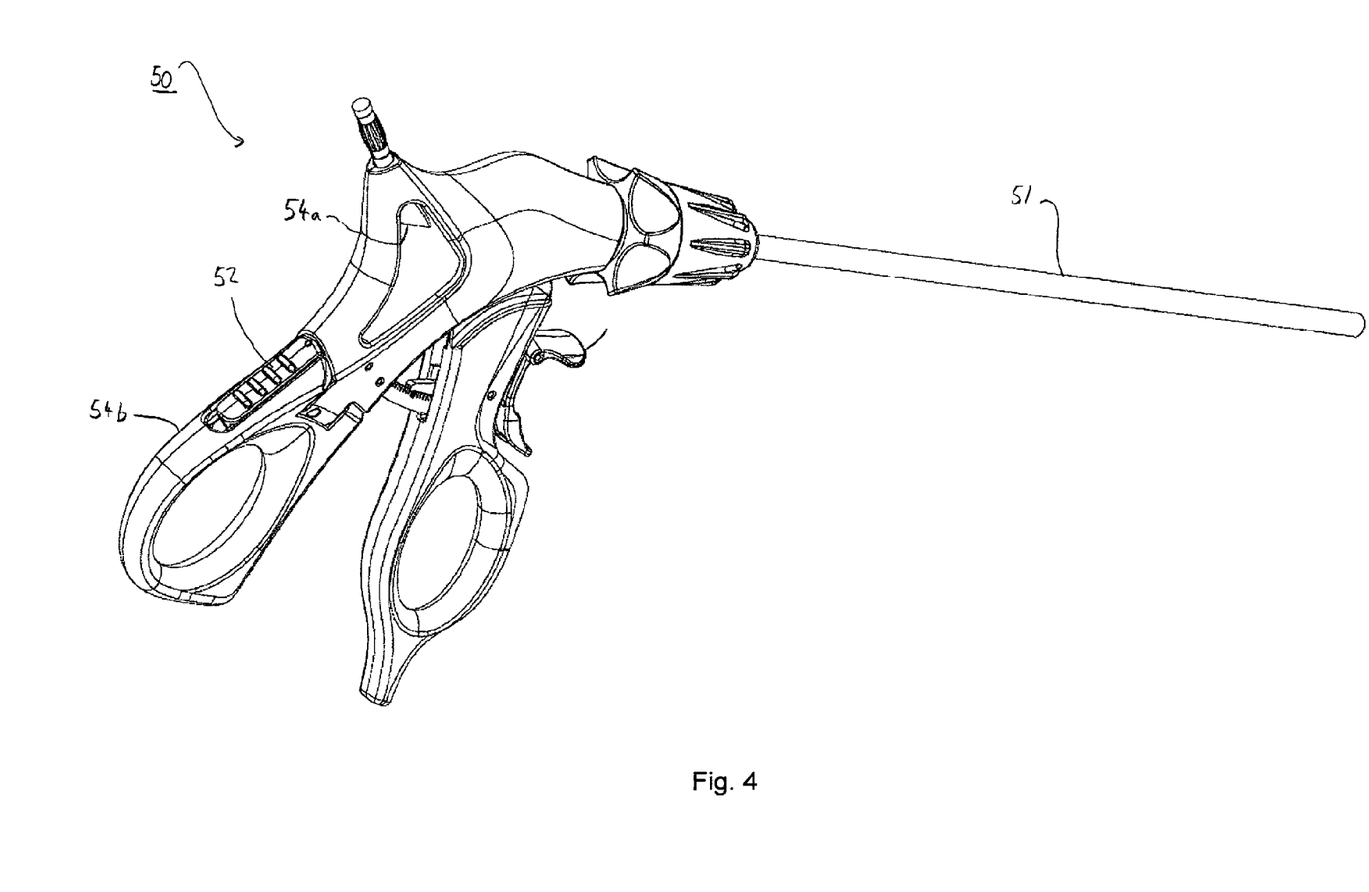
FIG. 4 depicts a perspective view of a second embodiment of a handle according to the present invention, attached to the shaft of a surgical instrument.

A second embodiment of the present invention is depicted in FIG. 4. This embodiment uses a slider mechanism to lock the angle of the end portion relative to the main portion. The construction of this embodiment is the same as the first embodiment, save as described below.

Figure 5A:
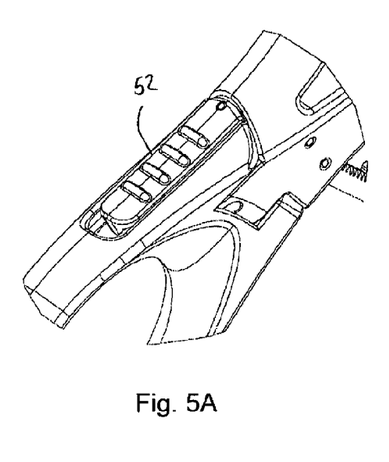
FIGS. 5A and 5B depict the handle of FIG. 4 in locked and unlocked configurations, respectively.
Figure 5B:
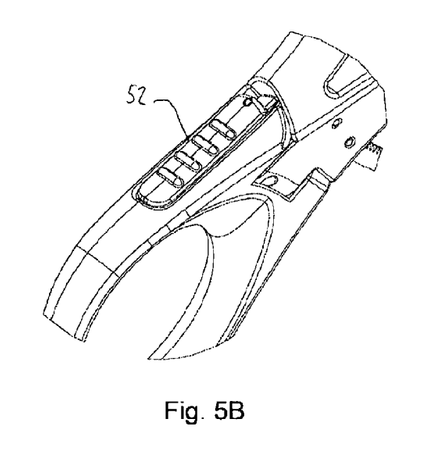

FIG. 4 depicts a perspective view of a second embodiment of a handle 50 according to the invention. The handle 50 includes a slider 52 for locking relative movement of the end portion 54b relative to the main portion 54a. The handle 50 is shown attached to the shaft 51 of a surgical instrument. FIGS. 5A and 5B are partial perspective views of the handle 50, showing the slider 52 in the locked position (FIG. 5A) and the unlocked position (FIG. 5B).

Figure 6:
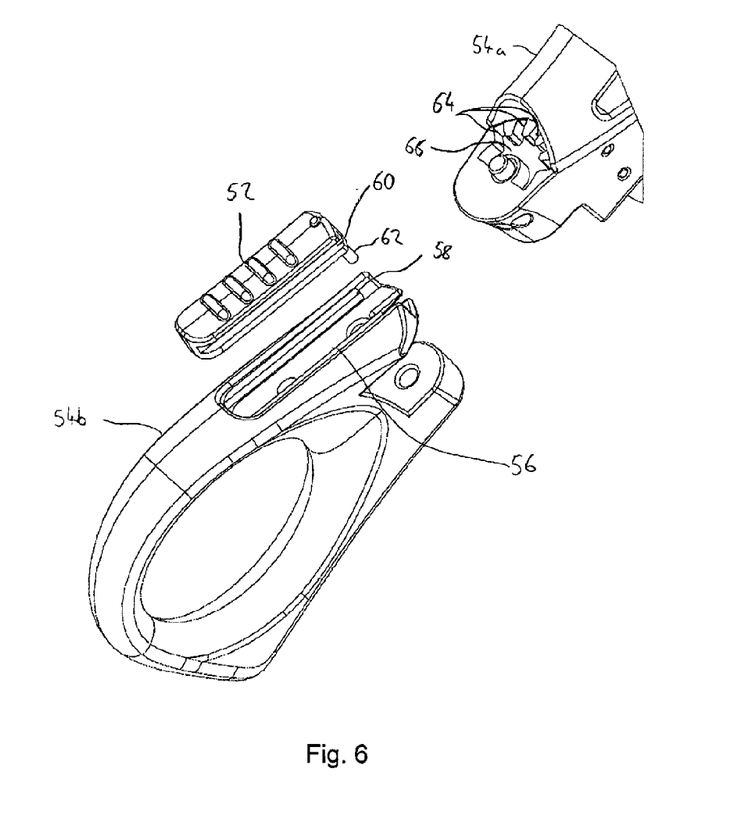
FIG. 6 depicts an exploded view of the locking mechanism of the handle of FIG. 4.

An exploded view of the locking mechanism of the second embodiment is depicted in FIG. 6. The slider 52 is received in a generally cuboid-shaped opening 56 formed in the end portion 54b. The opening 56 has longitudinal projections 58 formed in its side walls that engage corresponding grooves 60 formed in the edge of the slider 52, so that the slider 52 is retained on the end portion 54b by the engagement of the longitudinal projections 58 with the grooves 60 and can slide relative to the end portion 54b. A locking projection 62 extends from the end of the slider 52. On the main portion 54a, a series of recesses 64 are formed to receive the projection 62. A space 66 is provided before the recesses 64 begin. The recesses 64 are aligned with the indexing positions provided by the indexing means.

In use, the locking mechanism of this embodiment is operated by sliding the slider 52 towards or away from the main portion 54a. When the slider is moved away from the main portion 54a, the locking mechanism is in the unlocked position and the projection 62 is in the space 66, allowing movement of the end portion 54b relative to the main portion 54a. When the slider 52 is moved towards the main portion 54a, the locking mechanism is in the locked position and the projection 62 engages a recess 64 and prevents movement of the end portion 54b relative to the main portion 54a.

In an alternative construction of the embodiment of FIG. 4, a resilient member, for example a spring (not illustrated), is provided in the end portion 54b. This provides a force that acts on the slider 52 to urge it towards the locked position. With this alternative construction, the force provided by the spring will act to keep the slider 52 in the locked position in the absence of a force applied to the slider by a user.

In a further variation of the construction, holding means (not illustrated) can be provided in the handle and slider that interact to hold the slider 52 in the unlocked position when it has been moved away from the locked position by a predetermined amount. For example a protrusion and corresponding recess can be provided. With this variation the user can choose to use the spring biasing of the slider 52 by not moving the slider 52 far out of the locked position, or avoid the spring biasing by moving the slider 52 far enough out of the locked position to engage the holding means.

Figure 8:
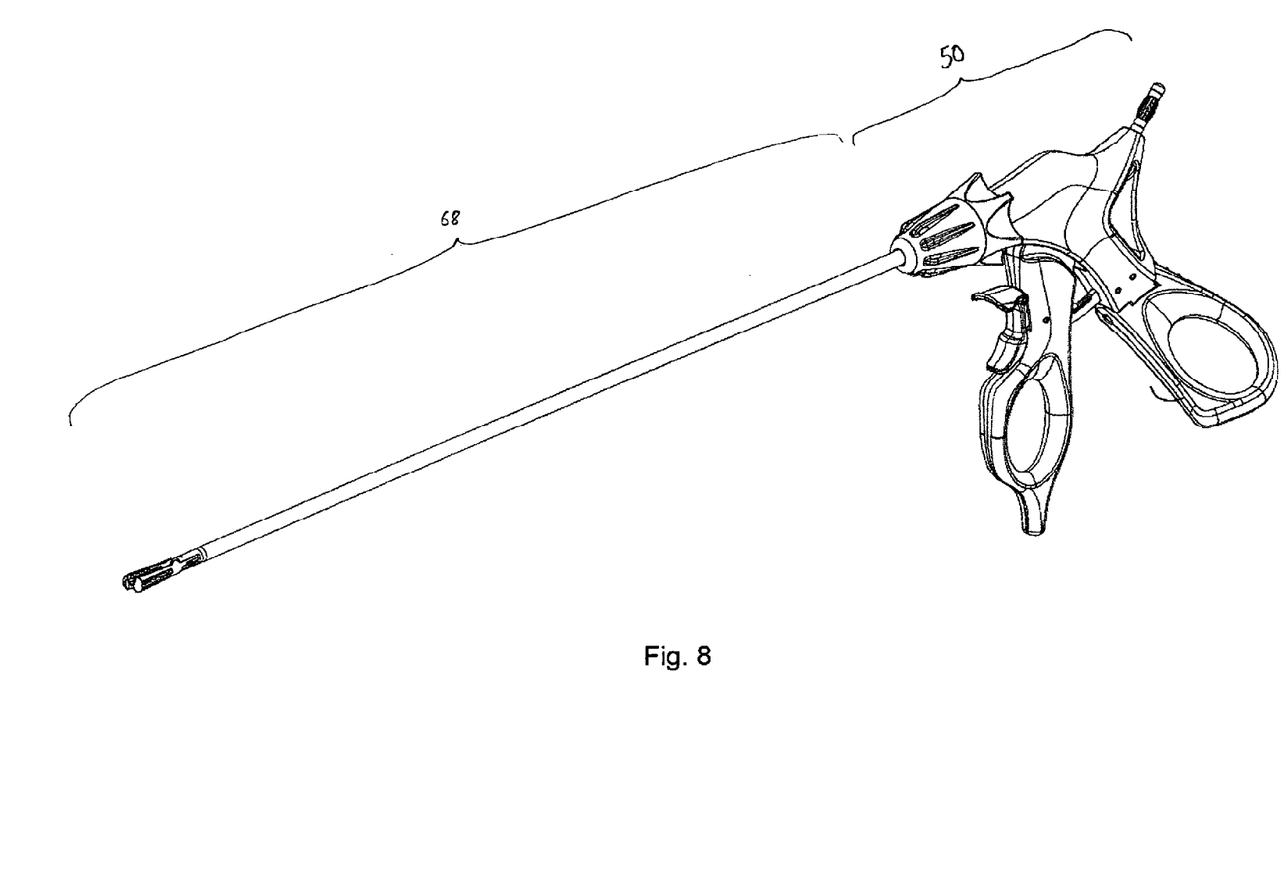
FIG. 8 depicts one example of a surgical instrument assembly using the handle of the present invention.

One example of a surgical instrument assembly according to the present invention is depicted in FIG. 8. As depicted in the FIG. 8 the handle of the FIG. 4 embodiment is connected to a single use "clinching" insert tool 68. It will be appreciated that the assembly could use any other surgical instrument for use in keyhole surgery, endoscopic or laparoscopic techniques.

Although specific locking and indexing mechanisms have been described in the embodiments above, the invention is not limited to such mechanisms.

The embodiments described above provide a combined indexing and locking mechanism. However, in alternative embodiments, the indexing features may provided without locking features and the locking features may be provided without indexing features.

The invention claimed is:

1. A handle for a surgical instrument, the handle comprising:
    (a) a first part comprising:
        a main portion; and
        an end portion which is pivotally connected to the main portion;
    (b) a second part which is pivotally connected to the main portion of the first part such that the first and second parts can move relative to each other;
    (c) an indexing mechanism for defining predetermined positions of the end portion relative to the main portion and for retaining the end portion in one of the predetermined positions, the indexing mechanism comprising a series of depressions spaced apart from each other formed in the main portion and a bearing retained in the end portion, wherein the bearing is resiliently biased towards the main portion and engages one of the series of depressions to provide the indexing; and
    (d) a locking mechanism configured to be movable between locked and unlocked positions, and wherein in the locked position the end portion is prevented from moving relative to the main portion;
    wherein the second part and the end portion of the first part each comprise an opening for receiving one or more of a user's digits 2. The handle according to claim 1, wherein the bearing is spherical.

3. The handle according to claim 1, wherein the locking mechanism comprises a shaft having a longitudinal projection configured to engage a corresponding recess formed in the end portion and, in the locked position, to also engage a corresponding recess formed in the main portion.

4. The handle according to claim 3, wherein the shaft forms the axis about which the end portion pivots relative to the main portion.

5. The handle according to claim 1, wherein the locking mechanism comprises a slider provided on the end portion, wherein the slider has a protrusion that, in the locked position, engages a corresponding recess formed in the main portion.

6. The handle according to claim 1, further comprising a ratchet for allowing movement of the first part towards the second part and for resisting movement of the first part away from the second part.

7. The handle according to claim 6, further comprising a trigger configured to engage a pawl of the ratchet and for disengaging the ratchet when pressed.

8. The handle according to claim 7, further comprising a ratchet disengaging lever connected to the trigger and movable between a first position, in which the trigger must be pressed to disengage the ratchet, and a second position, in which the ratchet is disengaged, wherein the ratchet disengaging lever is flush with the surface of the trigger when in the second position.

9. The handle according to claim 8, wherein the ratchet disengaging lever comprises at least one extension for enabling a user to move the lever from the second position to the first position.

10. The handle according to claim 1, wherein relative movement of the first and second parts causes operation of the surgical instrument.

11. The handle according to claim 10, wherein the surgical instrument is releasably connected to the handle.

12. The handle according to claim 11, further comprising connecting means allowing for the releasable connection of different surgical instruments.

* * * * *

UNITED STATES PATENT AND TRADEMARK OFFICE
CERTIFICATE OF CORRECTION

PATENT NO. : 8,551,077 B2  Page 1 of 1
APPLICATION NO. : 12/919576
DATED : October 8, 2013
INVENTOR(S) : David Main It is certified that error appears in the above-identified patent and that said Letters Patent is hereby corrected as shown below:

IN THE SPECIFICATION:

COLUMN 1 LINE 7 DELETE "371U.S." AND INSERT -- 371 U.S. --

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO.       : 8,551,077 B2                              Page 1 of 1
APPLICATION NO.  : 12/919576
DATED            : October 8, 2013
INVENTOR(S)      : David Main It is certified that error appears in the above-identified patent and that said Letters Patent is hereby corrected as shown below:

IN THE SPECIFICATION:

COL. 1   LINE 50    Delete "al)" and insert --al.)--

COL. 4   LINE 52    Delete "on" and insert --one--

COL. 5   LINE 25    Delete "20" and insert --4a--

IN THE CLAIMS:

COL. 8   LINE 11    After "digits" insert --.--

Signed and Sealed this
Twenty-ninth Day of April, 2014

Michelle K. Lee
*Deputy Director of the United States Patent and Trademark Office*